United States Patent
Podhajsky

(10) Patent No.: US 9,375,246 B2
(45) Date of Patent: Jun. 28, 2016

(54) SYSTEM AND METHOD OF USING THERMAL AND ELECTRICAL CONDUCTIVITY OF TISSUE

(75) Inventor: Ronald J. Podhajsky, Boulder, CO (US)

(73) Assignee: Covidien LP, Mansfield, MA (US)

( * ) Notice: Subject to any disclaimer, the term of this patent is extended or adjusted under 35 U.S.C. 154(b) by 1057 days.

(21) Appl. No.: 12/016,761

(22) Filed: Jan. 18, 2008

(65) Prior Publication Data

US 2008/0177199 A1   Jul. 24, 2008

Related U.S. Application Data

(60) Provisional application No. 60/881,238, filed on Jan. 19, 2007.

(51) Int. Cl.
| | |
|---|---|
| *A61B 18/18* | (2006.01) |
| *A61B 18/12* | (2006.01) |
| *A61B 5/01* | (2006.01) |
| *G01N 25/18* | (2006.01) |

(Continued)

(52) U.S. Cl.
CPC . *A61B 18/12* (2013.01); *A61B 5/01* (2013.01); *G01N 25/18* (2013.01); *G01N 27/045* (2013.01); *G01N 27/18* (2013.01); *A61B 5/053* (2013.01); *A61B 2017/00026* (2013.01); *A61B 2018/00875* (2013.01); *Y10T 29/49* (2015.01); *Y10T 29/49002* (2015.01); *Y10T 29/49007* (2015.01)

(58) Field of Classification Search
CPC .......... A61B 5/01; A61B 18/12; A61B 19/50; A61B 2018/00875; A61B 2017/0026; A61B 5/053

USPC ................ 606/27–32; 600/457; 607/101
See application file for complete search history.

(56) References Cited

U.S. PATENT DOCUMENTS

| | | | |
|---|---|---|---|
| 4,038,975 A | 8/1977 | Vrana et al. | |
| 4,291,708 A | 9/1981 | Frei et al. | |

(Continued)

FOREIGN PATENT DOCUMENTS

| | | |
|---|---|---|
| DE | 3711511 | 6/1988 |
| DE | 102004022206 | 12/2005 |

(Continued)

OTHER PUBLICATIONS

U.S. Appl. No. 12/016,754, Mahajan et al.

(Continued)

*Primary Examiner* — Michael Peffley
*Assistant Examiner* — Amanda Zink

(57) ABSTRACT

A system for planning, performing and/or evaluating the effectiveness of a therapeutic treatment of a target tissue is provided. The system includes at least one of a thermal conductivity probe including a microprobe sensor configured and adapted to measure a thermal conductivity in the target tissue in at least one direction and an electrical conductivity probe including a microprobe sensor configured and adapted to measure an electrical conductivity in the target tissue in at least one direction. The system further includes a multimeter operatively connected to at least one of the thermal conductivity probe and the electrical conductivity probe, the multimeter being configured and adapted to deliver energy to at least one of the thermal conductivity probe and the electrical conductivity probe and a computer operatively connected to the multimeter.

4 Claims, 3 Drawing Sheets

(51) Int. Cl.
*G01N 27/04* (2006.01)
*G01N 27/18* (2006.01)
*A61B 5/053* (2006.01)
*A61B 17/00* (2006.01)
*A61B 18/00* (2006.01)

(56) References Cited

U.S. PATENT DOCUMENTS

| | | | |
|---|---|---|---|
| 4,380,237 A * | 4/1983 | Newbower | 600/506 |
| 4,537,203 A | 8/1985 | Machida | |
| 4,595,012 A * | 6/1986 | Webler et al. | 600/374 |
| 4,617,939 A | 10/1986 | Brown et al. | |
| 4,719,441 A | 1/1988 | Horn | |
| 4,729,385 A | 3/1988 | Juncosa et al. | |
| 4,902,138 A | 2/1990 | Goeldner | |
| 4,955,383 A | 9/1990 | Faupel | |
| 4,966,158 A | 10/1990 | Honma et al. | |
| 5,184,620 A | 2/1993 | Cudahy et al. | |
| 5,184,624 A | 2/1993 | Brown et al. | |
| 5,217,014 A | 6/1993 | Hahn et al. | |
| 5,320,101 A | 6/1994 | Faupel et al. | |
| 5,353,802 A | 10/1994 | Ollman | |
| 5,630,426 A * | 5/1997 | Eggers et al. | 600/547 |
| 5,704,355 A | 1/1998 | Bridges | |
| 5,722,401 A * | 3/1998 | Pietroski | A61B 5/0422 600/374 |
| 5,800,350 A | 9/1998 | Coppleson et al. | |
| 5,904,709 A * | 5/1999 | Arndt et al. | 607/101 |
| 6,026,323 A | 2/2000 | Skladnev et al. | |
| 6,047,216 A | 4/2000 | Carl | |
| 6,092,528 A | 7/2000 | Edwards | |
| 6,134,476 A | 10/2000 | Arndt | |
| 6,175,768 B1 | 1/2001 | Arndt | |
| 6,241,725 B1 * | 6/2001 | Cosman | 606/41 |
| 6,524,308 B1 | 2/2003 | Muller et al. | |
| 6,645,198 B1 | 11/2003 | Bommannan | |
| 6,668,230 B2 | 12/2003 | Mansky et al. | |
| 6,845,264 B1 | 1/2005 | Skladnev et al. | |
| 7,869,854 B2 | 1/2011 | Shachar | |
| 2003/0013986 A1 * | 1/2003 | Saadat | A61B 5/015 600/549 |
| 2003/0195588 A1 * | 10/2003 | Fischell et al. | 607/55 |
| 2004/0015162 A1 | 1/2004 | McGaffigan | |
| 2004/0193021 A1 | 9/2004 | Zdeblick | |
| 2007/0197891 A1 | 8/2007 | Shachar | |
| 2009/0082831 A1 * | 3/2009 | Paul et al. | 607/59 |
| 2010/0198282 A1 * | 8/2010 | Rogers | 607/3 |

FOREIGN PATENT DOCUMENTS

| | | |
|---|---|---|
| DE | 202005015147 | 2/2006 |
| EP | 0558429 | 9/1993 |
| EP | 1 462 065 | 9/2004 |
| WO | WO 9944520 | 9/1999 |
| WO | WO 0054682 | 9/2000 |
| WO | WO 0070333 | 11/2000 |
| WO | WO 2004052182 | 6/2004 |
| WO | WO 2007/010059 | 9/2007 |

OTHER PUBLICATIONS

European Search Report for European Application No. 08001016.8 dated Mar. 11, 2008.
European Search Report for European Application No. 08001019.2 dated Sep. 8, 2008.
Extended European Search Report corresponding to EP 11 17 6684.6, completed Oct. 31, 2013 and mailed Nov. 7, 2013; (5 pp).
Extended European Search Report corresponding to EP 11 17 6685.3, completed Oct. 31, 2013 and mailed Nov. 7, 2013; (6 pp).
Ming Yi et al., "Micromachined Electrical Conductivity Probe for RF Ablations of Tumors", *Proceedings of the 2005 ASME Int'l Mechanical Engineering Congress and Exposition*; Nov. 5, 2005; pp. 53-56.

* cited by examiner

SYSTEM AND METHOD OF USING THERMAL AND ELECTRICAL CONDUCTIVITY OF TISSUE

CROSS-REFERENCE TO RELATED APPLICATION

The present application claims the benefit of and priority to U.S. Provisional Application Ser. No. 60/881,238, filed on Jan. 19, 2007, the entire content of which is incorporated herein by reference.

BACKGROUND

1. Technical Field

The present disclosure relates to electrosurgical instruments, systems and methods of using the same and, more particularly, the present disclosure relates to systems and methods for sensing and using directional attributes of tissue.

2. Discussion of Related Art

Thermal therapy, such as Radiofrequency (RF) ablation, is an effective procedure for the treatment of certain tumors and the like. However, the outcome of said thermal therapies may be unpredictable and inconsistent. The increasing use of thermal therapy in the treatment of biological tissue and the like necessitates an accurate determination and a thorough understanding of the unpredictability and inconsistencies associated with thermal therapy. It is believed that thermal conductivity and electrical conductivity of biological tissues is a factor in contributing to said unpredictability and inconsistencies associated with thermal therapy.

It has been seen that biological tissue has different thermal and/or electrical conductivities in different directions. Thermal conductivity of biological tissues is dependant of the particular type of biological tissue and on the composition of the biological tissue. Different biological tissues exhibit different and/or unique thermal conductivities based on factors such as tissue density, tissue hydration, vascularization, age, direction and distance to major blood vessels, etc. Additionally, different biological tissues may exhibit a different and/or unique thermal conductivity in various directions from one another.

Electrical conductivity is not only determined by tissue type and composition, but also by other externally applied physical and chemical influences during thermal treatment, such as, for example, temperature inducement and saline pretreatment. An accurate knowledge of a change in the electrical conductivity of the target tissue, due to temperature elevation, may be a factor in predicting ablation area/volume, RF power control, and optimization of the cyclic RF power delivery. Knowledge of electrical conductivity as a function of salinity level of the target tissue may be another factor in predicting ablation area/volume, RF power control, and optimization of the cyclic RF power delivery.

These differences in thermal and electrical conductivity may affect the shape of the treatment zone during thermal therapies. Knowledge of the thermal and electrical conductivity of the tissue may also be used to enhance the resolution of modern imaging modalities (fluoroscopy, X-ray, CT scan, MRI, Ultrasound, etc.). Accordingly, sensing, measuring and interpreting these values and differences in thermal and/or electrical conductivities would be useful in assisting in the planning and performing of thermal therapy procedures.

SUMMARY

A system for planning, performing and/or evaluating the effectiveness of a therapeutic treatment of a target tissue is provided. The system includes at least one of a thermal conductivity probe including a microprobe sensor configured and adapted to measure a thermal conductivity in the target tissue in at least one direction and an electrical conductivity probe including a microprobe sensor configured and adapted to measure an electrical conductivity in the target tissue in at least one direction. The system further includes a multimeter operatively connected to at least one of the thermal conductivity probe and the electrical conductivity probe, the multimeter being configured and adapted to deliver energy to at least one of the thermal conductivity probe and the electrical conductivity probe and a computer operatively connected to the multimeter.

The system may further include a power supply operatively connected to each of the thermal conductivity probe and the electrical conductivity probe. The power supply may be configured and adapted to supply power to each of the thermal conductivity probe and the electrical conductivity probe. The system may further include a therapeutic treatment device configured and adapted to deliver therapeutic energy to the target tissue. The energy delivery setting of the therapeutic treatment device may be determined based on at least one of the thermal and electrical conductivity measurements.

The system may further include an indicator for providing an indication in response to a predetermined value of at least one of the thermal and electrical conductivity measurements, whereby critical tissue can be kept from undue harm.

Also provided is a method of planning, performing and/or evaluating the effectiveness of a therapeutic treatment of a target tissue. The method includes measuring at least one of the thermal and electrical conductivity of a target tissue in at least one direction, inputting at least one of the measured conductivities of the target tissue for each direction into a modeling environment, creating a representation of a treatment zone for the target tissue from the modeling environment, and selecting at least one therapeutic treatment device, at least one energy setting for the therapeutic treatment device, and an orientation for the therapeutic treatment device based on the representation of the treatment zone for the target tissue.

The method may further include measuring both thermal and electrical conductivity of a target tissue in at least one direction. Additionally, the method include treating the tissue using the at least one therapeutic treatment device. The method may also include measuring at least one of the thermal and electrical conductivity of a target tissue in at least one direction following treatment of the target tissue. The method may further include measuring at least one of the thermal and electrical conductivity of a target tissue in multiple directions.

The method may further include the step of providing an indication in response to a predetermined value of at least one of the thermal and electrical conductivity measurements, whereby critical tissue can be kept from undue harm.

A method of enhancing an image is also provided. The method includes measuring at least one of a thermal conductivity and an electrical conductivity of a target tissue in at least one direction, inputting at least one of the measured conductivities of the target tissue for each direction into a modeling environment to create at least one resulting image, and combining the at least one resulting image to produce an enhanced image. The imagining technique may include at least one of fluoroscopy, X-ray, CT scan, ultrasound, and MRI.

Also provided is a system for planning, performing and/or evaluating the effectiveness of a therapeutic treatment of a target tissue, including at least one of a thermal conductivity probe and an electrical conductivity probe. Each of the thermal conductivity and the electrical conductivity probes include at least one microprobe sensor, and the microprobe sensors measure a respective thermal conductivity and electrical conductivity of the target tissue. The system further includes a multimeter operatively connected to at least one of the thermal conductivity probe and the electrical conductivity probe, the multimeter being configured and adapted to deliver energy to at least one of the thermal conductivity probe and the electrical conductivity probe and a computer operatively connected to the multimeter. Each microprobe sensor may measure a respective property in at least one direction.

The system may further include a power supply operatively connected to each of the thermal conductivity probe and the electrical conductivity probe. The power supply may power each of the thermal conductivity probe and the electrical conductivity probe. The system may further include a therapeutic treatment device for delivering therapeutic energy to the target tissue. The energy delivery setting of the therapeutic treatment device may be determined based on at least one of the thermal and electrical conductivity measurements gathered by the respective thermal and electrical conductivity probes.

DETAILED DESCRIPTION OF THE DRAWINGS

Embodiments of the present disclosure are disclosed herein with reference to the drawings, wherein.

DETAILED DESCRIPTION OF EMBODIMENTS

Figure 1:
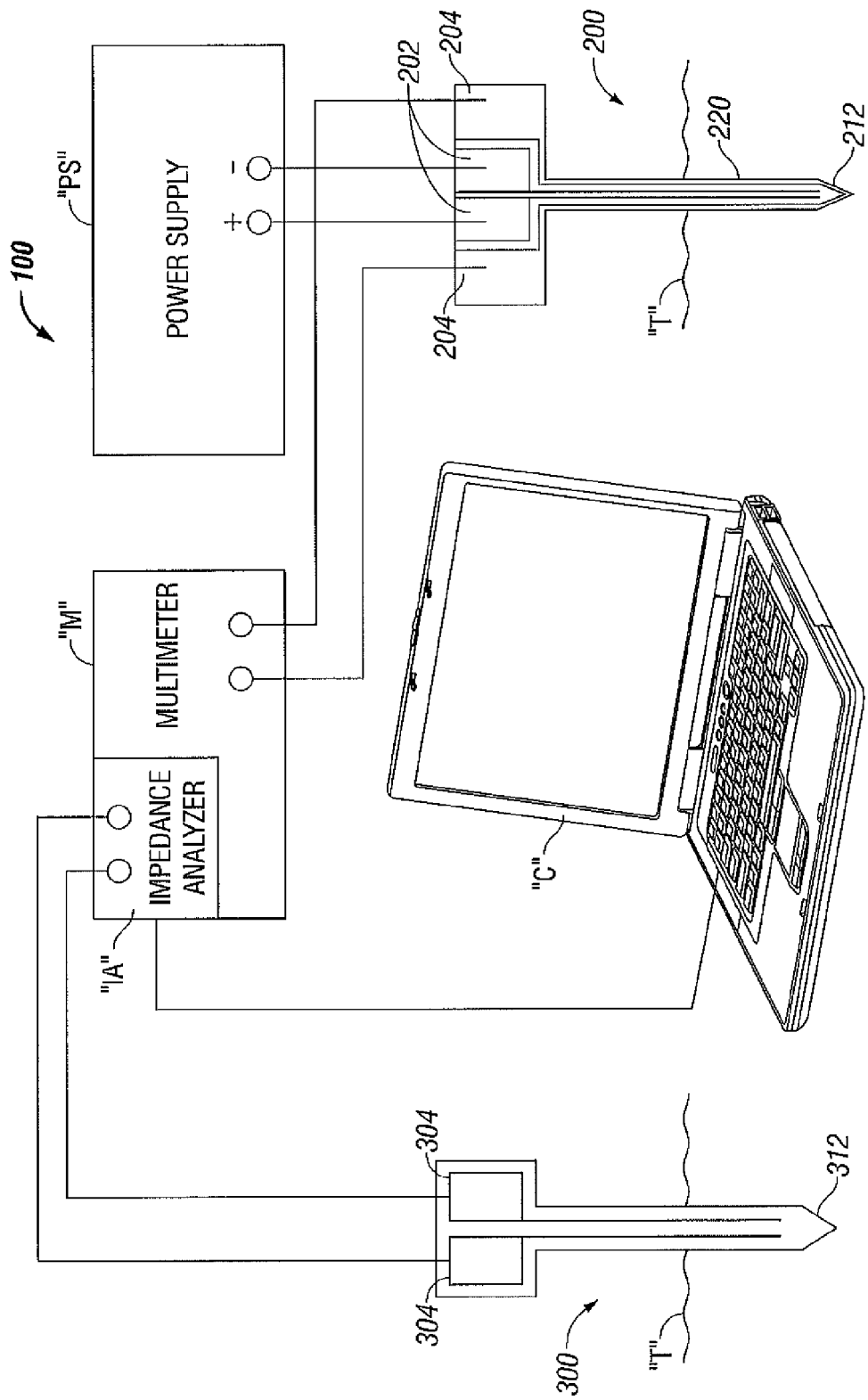
FIG. 1 is a schematic perspective view of a conductivity sensing system according to an embodiment of the present disclosure.
Figure 2:
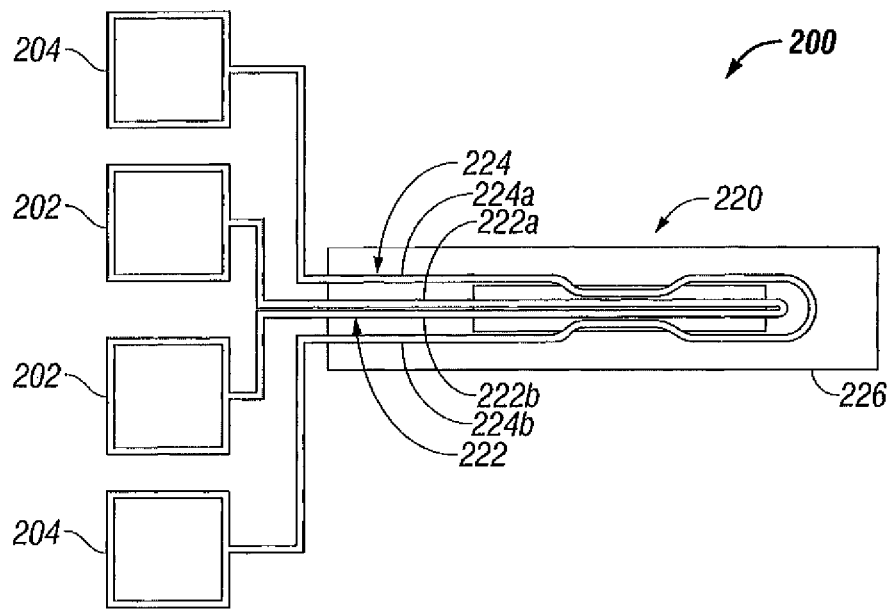
FIG. 2 is a schematic illustration of an embodiment of a thermal conductivity sensing device of the conductivity sensing system of FIG. 1.
Figure 3:
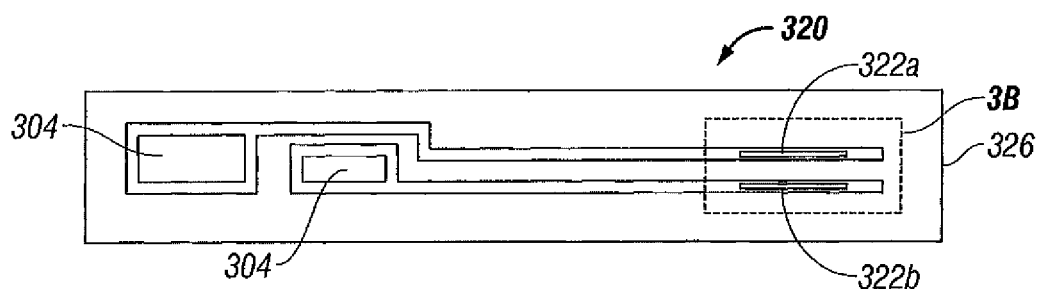
FIG. 3 is a schematic illustration of an embodiment of an electrical conductivity sensing device of the system of FIG. 1.
Figure 3A:
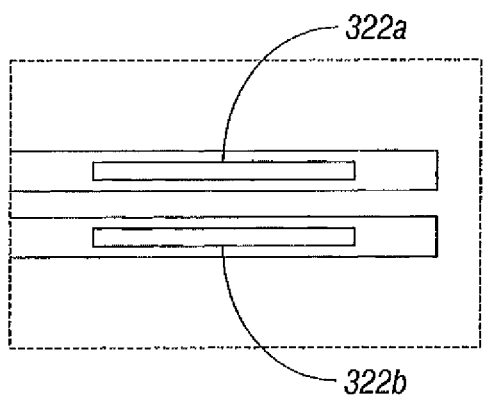
FIG. 3A is an enlarged view of the indicated area of detail of FIG. 3.

The devices, systems and methods of the present disclosure provide for the sensing of directional attributes of tissue in order to assist in planning, performing and/or evaluating the effectiveness of thermal therapy procedures. In the drawings and in the description which follows, the term "proximal", as is traditional, will refer to the end of the system, or component thereof, which is closest to the operator, and the term "distalt" will refer to the end of the system, or component thereof, which is more remote from the operator.

As used herein, the term "thermal treatment" is understood to include and is not limited to treatment using radio-frequency (RF), laser, microwave, cryoablation ultrasound, HIFU, and electromagnetic stimulation of micro- and nanoparticles.

1. Electrosurgical System

With reference to FIG. 1, in accordance with an embodiment of the present disclosure, a conductivity sensing system for sensing directional attributes of tissue in order to help in planning, performing and evaluating the effectiveness of thermal therapy, ablation and other electrosurgical procedures, is generally designated as 100. System 100 includes a sensing device 200 in the form of a thermal conductivity probe, a power source "PS" connected to or connectable to device 200, a multimeter "M" or impedance analyzer "IA" connected to or connectable to device 200 and a computer "C" connected to or connectable to multimeter "M". System 100 may further include another electrosurgical device 300 in the form of an electrical conductivity probe, connected to or connectable to multimeter "M", an impedance analyzer "IA" or the like, or other suitable devices.

As seen in FIG. 1, thermal conductivity probe 200 includes a first pair of bonding pads 202 electrically connected to or electrically connectable to a power source "PS", and a second pair of bonding pads 204 electrically connected to or electrically connectable to multimeter "M". Electrical conductivity probe 300 may include a pair of bonding pads 304 electrically connected to or electrically connectable to multimeter "M". The aspects of the present disclosure should not be read as limited to the embodiments of thermal conductivity probe 200 and electrical conductivity probe 300 described herein. Any probe or probes capable of acquiring directional attributes of tissue have been envisioned for use with aspects of the present disclosure. For a more detailed discussion thermal conductivity probe 200 and electrical conductivity probe 300, as shown, including methods of manufacture and use, please refer to commonly owned U.S. patent application Ser. No. 60/881238, entitled "Thermal and Electrical Conductivity Probes and Methods of Making the Same", filed concurrently herewith, the contents of which are hereby incorporated by reference in their entirety.

Figure 4:
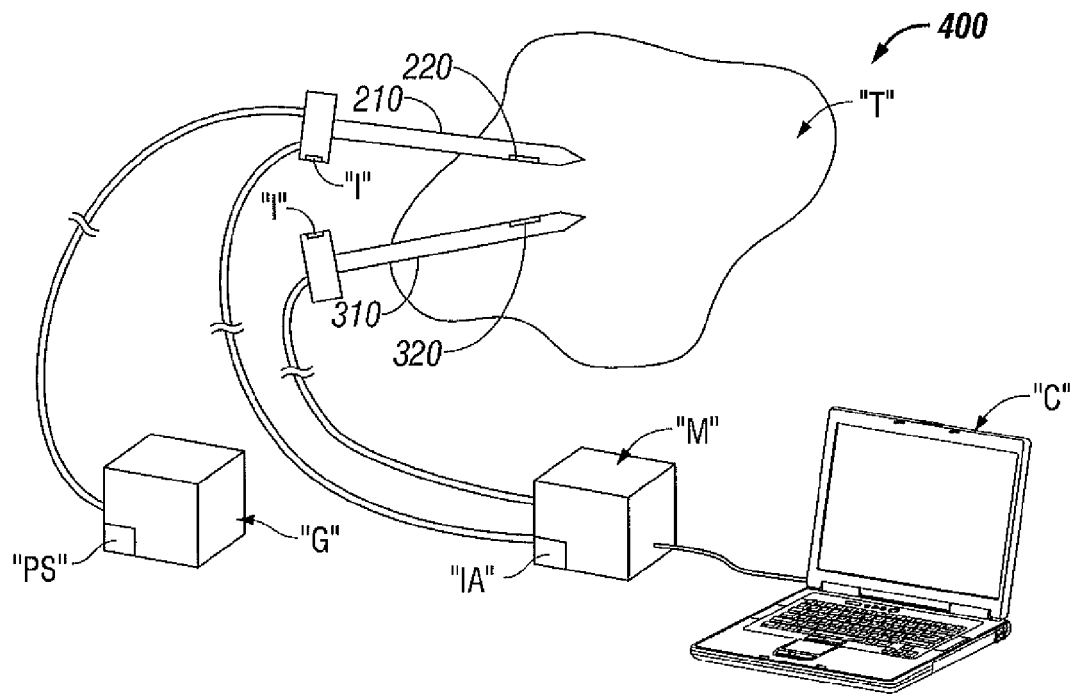
FIG. 4 is a schematic illustration of the conductivity sensing circuits of FIG. 1, shown mounted on electrosurgical devices in operative association with a target tissue.

As seen in FIG. 4, in an alternate embodiment of the present disclosure, conductivity sensing system 100 is incorporated into an electrosurgical system 400 for performing electrosurgical procedures. Electrosurgical system 400 includes a generator "G", for example, an AC or DC power supply, a radiofrequency generator providing energy at frequencies between several kilohertz to several hundred megahertz, or any other suitable power source. Generator "G" may have a power output ranging from several watts to several hundred watts, depending on the clinical need. Generator "G" may have control devices to increase or modulate power output as well as readout and display devices to monitor energy parameters such as voltage, current, power, frequency, temperature, impedance, etc., as appreciated by one skilled in the art. Other types of power sources and/or generators are contemplated, e.g., including and not limited to resistive heating units, laser sources, or microwave generators. Generator "G" includes power source "PS" capable of supplying constant power to microprobe sensor 220. Other types of power sources and/or generators are contemplated, e.g., including and not limited to resistive heating units, laser sources, or microwave generators.

2. Method of Using Thermal Conductivity

Knowledge of the thermal conductivity of the tissue permits a surgeon to adapt the treatment based on the thermal conductivity of that tissue. For example, a measurement of a relatively low thermal conductivity would indicate that, during therapeutic treatment of tissue, that thermal energy would travel relatively less in the direction in which the relatively low thermal conductivity measurement was made as compared to other directions. Likewise, a measurement of a relatively high thermal conductivity would indicate that, during therapeutic treatment of tissue, that thermal energy would travel relatively more in the direction in which the relatively high thermal conductivity measurement was made as compared to other directions.

As such, once the thermal conductivity of the target tissue "T" is determined, a selection of a suitable electrosurgical ablation needle, for example, associated power parameters, and relative orientations of ablation needle placement may be determined, based thereon, for the therapeutic treatment of the target tissue "T" by the electrosurgical ablation needle. The thermal conductivity of the target tissue "T" may be acquired intermittently throughout the treatment of the tissue. In this manner, a surgeon may monitor the effects of the treatment on said target tissue "T" and the surrounding tissue.

Thermal conductivity probe 200 is adapted to measure thermal conductance $K_{eff}$ as represented by the following equation as commonly known in the field:

$$K_{eff} = K\left\{1 + \frac{n[(\rho c)_b \pi r_b^2 \overline{V} \cos\gamma]^2}{\sigma_\Delta K^2}\right\} + q_{met}$$

where:
   $K_{eff}$—is the "effective" tissue conductance which is measured. $K_{eff}$ is the combination of conduction (due to intrinsic thermal conductivity) and convection (due to perfusion);
   K—is tissue conductance in the absence of perfusion;
   n—is the number of blood vessels;
   p—in $(\rho c)_b$ is the density of blood;
   c—in $(\rho c)_b$ is the specific heat of blood;
   $r_b$—is vessel radius;
   V—is the blood flow velocity vector within the vessel;
   γ—is the relative angle between blood vessel direction and tissue temperature gradient;
   σΔ—is a shape factor term; and
   $q_{met}$—is metabolic heat generation.

Knowledge of the thermal conductivity of the tissue can also be useful in identifying and locating organs, vessels, ducts, etc. As can be understood from the above equation for determining thermal conductivity, as fluid flows through various tissue structures, the diameter of the structure and the flow rate of the fluid therethrough affect the thermal conductivity of the tissue. The differences in thermal conductivity between the target tissue "T" and the surrounding organs, vessels, ducts, etc. may be used to locate and identify such structures. As will be discussed in further detail below, these thermal conductivity measurements may be incorporated into modern imaging techniques to enhance the resulting images. A warning system (not shown) may be incorporated into electrosurgical system 100 to alert a user as probe 200 approaches an organ, vessel, duct, etc. Theoretical and empirical data has shown that thermal conductivity, as opposed to electrical conductivity, may be better suited for identifying structures having instances of high flow rate therethrough.

3. Method of Using Electrical Conductivity

Knowledge of the electrical conductivity of the tissue permits a surgeon to adapt the treatment based on the electrical conductivity of that tissue. For example, a measurement of a relatively low electrical conductivity would indicate that, during therapeutic treatment of tissue, that electrical energy would travel relatively less in the direction in which the relatively low electrical conductivity measurement was made as compared to other directions. Likewise, a measurement of a relatively high electrical conductivity would indicate that, during therapeutic treatment of tissue, that electrical energy would travel relatively more in the direction in which the relatively high electrical conductivity measurement was made as compared to other directions.

Once the electrical conductivity of the target tissue "T" is determined, a selection of a suitable electrosurgical ablation needle, for example, associated power parameters, and relative orientations of ablation needle placement may be determined, based thereon, for the thermal treatment of said target tissue "T" by said electrosurgical ablation needle.

The extent, level and/or direction of electrical conductivity may be altered, varied and/or directed by increasing and/or decreasing the level of salinity in and around the target tissue.

The electrical conductivity of target tissue "T" may be continuously acquired throughout a thermal treatment procedure to continuously monitor the effect of the treatment on the target tissue "T" and the surrounding tissue. Alternatively, the electrical conductivity may be acquired intermittently or between thermal treatments. In this manner, the tissue to return to normal or non-excited state prior to acquiring the conductivity of the tissue, thereby minimizing the effect of the treatment has on the conductivity values.

Figure 5:
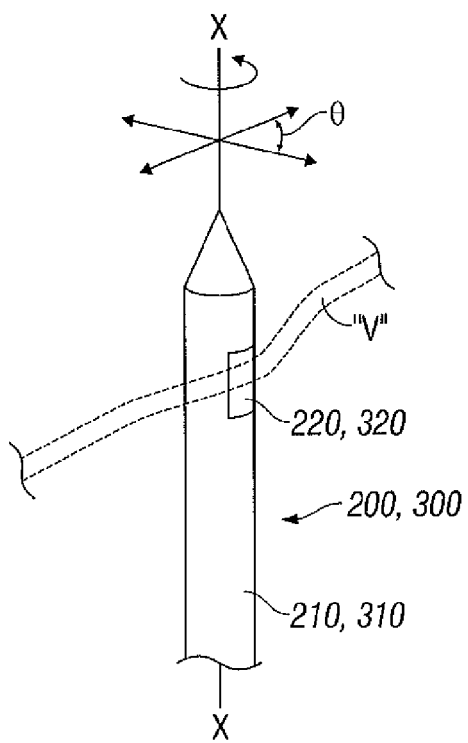
FIG. 5 is a perspective view of a distal end of an electrosurgical device of the present disclosure.

As with thermal conductivity, knowledge of the electrical conductivity of the tissue can also be useful in identifying local organs, vessels, ducts, etc. The differences in electrical conductivity between said target tissue "T" and the surrounding organs, vessels, ducts, etc., may be used to locate and identify such structures. Electrical conductivity measurements may also be incorporated into modern imaging techniques to enhance the image. A warning system (not shown) may be incorporated into electrosurgical system 100 to alert a user as probe 300 approaches an organ, vessel, duct, etc. Theoretical and empirical data shows that electrical conductivity may be better suited for identifying structures having instances of low flow rate therethrough. p 4. Method of Procedure Planning and Performing In accordance with the present disclosure, as seen in FIGS. 4 and 5, an electrosurgical system 400 may be used to plan, perform and/or evaluate the effectiveness of thermal therapy procedures and the like. According to a method of the present disclosure, electrosurgical device 210 and/or electrosurgical device 310 are introduced into a target tissue or target in-vivo tissue "T" using suitable surgical techniques. For example, device 210 and/or device 310 may be introduced into the target tissue "T" through percutaneous insertion through the skin of the patient and may be monitored or guided using suitable imaging techniques (e.g., fluoroscopy, X-ray, CT scan, MRI). In one embodiment, electrosurgical devices 210, 310 are ablation needles; however it is envisioned that the aspects of the present disclosure can be adapted for use with any suitable electrosurgical device.

With electrosurgical device 210 and/or electrosurgical device 300 positioned in the target tissue "T", electrosurgical device 210 and/or electrosurgical device 310 is/are activated, as described above, to sense, measure and/or otherwise determine a respective thermal conductivity and/or an electrical conductivity of the target tissue "T". In an embodiment, where microprobe sensor 220 of device 210 is located on one side thereof or where sensor 320 of device 310 is located on one side thereof, the respective thermal and electrical conductivities are measured in one particular direction (i.e., in the direction in which sensors 220 and/or 320 are directed). Alternatively, sensing devices 200, 300 may be used in a similar manner. Accordingly, in order to predict and/or plan a thermal therapy procedure, devices 210 and/or 310 may be rotated along a longitudinal axis "X" thereof, by a known angle, in order to measure the values of the thermal and electrical conductivities of target tissue "T" at each of the rotated angles.

Once the values of the thermal and electrical conductivities of target tissue "T" at each of the rotated angles is measured, a determination of the type of electrosurgical treatment device, the energy delivery parameters for the electrosurgical treatment device and/or the orientation of placement of the electrosurgical treatment device in the target tissue may be achieved. Such a determination is conducted in order to maximize the desired and/or needed therapeutic effects of the electrosurgical treatment device on the target tissue and to minimize any undesired and/or un-needed therapeutic effects of the electrosurgical treatment device on non-target tissue. As discussed in further detail below, the thermal and electrical conductivity values may also be used in conjunction with other imaging modalities to enhance the resolution of the image.

In one method, devices 210 and/or 310 are rotated a full 360° in order to measure the values of the thermal and electrical conductivities of target tissue "T" completely around devices 210 and/or 310. In one method, for example, the thermal and electrical conductivities of target tissue "T" may be measured and/or captured at approximately 90° angles with respect to one another. It is contemplated that, as seen in FIG. 5, the thermal and electrical conductivities of target tissue "T" may be measured and/or captured at any suitable and/or desired angle "Θ" relative to one another.

In an embodiment, a portion of device 210, 310, disposed outside of the target tissue and/or outside of the body may be marked with indicia "I" (see FIG. 4) that is axially aligned with respective sensors 220, 320. In this manner, the location/orientation/direction of sensors 220, 320 may be readily ascertained.

In one particular method, as seen in FIG. 5, devices 210, 310 may be inserted into target tissue "T" such that respective sensors 220, 320 are oriented or directed toward a major blood vessel "V". This particular orientation may be identified as the 0° orientation or the like. During the procedure, devices 210, 3 10 may be rotated about the respective longitudinal "X" axes to angles of approximately 90°, 180° and/or 270° relative to the 0° orientation.

Alternatively, an array of sensors may be placed facing the cardinal directions on devices 210 and/or 310 such that rotation is not necessary. Other array configurations would provided necessary resolution.

The measured values of the thermal and electrical conductivities of target tissue "T" provide the directional attributes of the target tissue "T" to a suitable processor, such as a computer, including a suitable simulation and/or modeling environment, The measured and/or captured values of the thermal and electrical conductivities of target tissue "T" serve as input parameters in the computer simulation/modeling environment, such as, for example, E-Therm, COMSOL™, available from COMSOL, Inc., Burlington, Mass., etc. or any suitable finite element modeling program, neural network environment, or model-based predictive control environment.

The measured values of the thermal and electrical conductivities of target tissue "T" would provide information about the target tissue "T" surrounding and/or in close proximity to devices 210, 310 that would determine the differential directivities of thermal and/or electrical conductivities that would become a part of an initial condition of the computer simulation. The computer simulation may then predict and display any non-uniform shape of the ablated coagulation zone as a numerical representation, a graphical representation, as an alarm that important dimensions are not met, or any other suitable indicator.

A graphical representation may be available as an input to a medical imaging device to be integrated into a medical image generated by any suitable imaging method, as described above. This data representation may be used for procedure planning by providing this essential information about said target tissue "T" prior to or during treatment to predict the shape of the treated zone. Similar data representation may also be acquired and used following a treatment to evaluate the effectiveness of the treatment. This predictive modeling with sensed conductivities may be used with suitable energy treatment modalities that include and are not limited to RFA (e.g. Cool-Tip), microwave antennas, cryoablation probes, and laser thermal devices.

As discussed above, the thermal and electrical conductivity values may be used to enhance other imaging modalities. For example, conductivity values may be useful in highlighting the presence and location of organs, vessels, ducts, etc. In this manner, a surgeon may plan and perform a procedure with a better understanding of said target tissue "T" and the location of critical structures in the area such that they may be avoided during treatment. Additionally, viewing the images enhanced through use of the conductivity values may expose structure that would otherwise have gone undetected. Conductivity values may also be useful in providing the degree of perfusion and/or vasculature in the target tissue.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of preferred embodiments. Those skilled in the art will envision other modifications within the scope and spirit of the claims appended hereto.

Although the above description has detailed the aspects of the present disclosure with regards to medical treatment, this method of directional conductivity measurement may apply to other fields of endeavor. For example, in the field of geology, this method could be used to detect subterranean features such as the presence of water, oil, rock or geological compositions.

What is claimed is:

1. A method for treating tissue, comprising:
    positioning a surgical device including at least one sensor into tissue of a patient;
    measuring, using the at least one sensor of the surgical device, at least one of a thermal conductivity or an electrical conductivity of the tissue at a known angle relative to a starting point of the surgical device, wherein measuring at least one of the thermal conductivity or the electrical conductivity of the tissue includes rotating the surgical device about a longitudinal axis defined by the surgical device by the known angle relative to the starting point to a first point, different than the starting point, while maintaining the surgical device in a straight configuration during its rotation from the starting point to the first point;
    inputting the at least one measured conductivity of the tissue into a modeling environment;
    generating a representation of a tissue treatment zone from the modeling environment;
    selecting an energy setting based on the representation of the tissue treatment zone; and
    delivering therapeutic energy to the tissue using the selected energy setting.

2. The method according to claim 1, further comprising rotating the surgical device about the longitudinal axis by the known angle relative to the first point to a second point and measuring at least one of the thermal conductivity or the electrical conductivity of the tissue at the second point, while maintaining the surgical device in the straight configuration during its rotation from the first point to the second point.

3. The method according to claim 1, further comprising selecting a positioning orientation of the surgical device based on the at least one measured conductivity of the tissue.

4. The method according to claim 1, further comprising providing an indication based on the at least one measured conductivity of the tissue.

\* \* \* \* \*